United States Patent [19]

Sugiyama et al.

[11] Patent Number: 5,153,308
[45] Date of Patent: Oct. 6, 1992

[54] S-SULFONATED CALCITONIN DERIVATIVES

[75] Inventors: Takashi Sugiyama; Takashi Kamimura, both of Hino; Kenichi Masuda, Hachioji; Yoji Suzuki, Hino, all of Japan

[73] Assignee: Teijin Limited, Osaka, Japan

[21] Appl. No.: 362,855

[22] Filed: Jun. 7, 1989

[30] Foreign Application Priority Data

Jun. 16, 1988 [JP] Japan ............................. 63-146961
Oct. 19, 1988 [JP] Japan ............................. 63-318476

[51] Int. Cl.$^5$ .................. A61K 37/02; A61K 37/30; C07K 5/00; C07K 7/00
[52] U.S. Cl. .................................. 530/307; 530/345
[58] Field of Search .................. 530/307, 345; 514/12

[56] References Cited

U.S. PATENT DOCUMENTS

| | | | |
|---|---|---|---|
| 4,212,795 | 7/1980 | Hughes et al. | 260/112.5 T |
| 4,658,014 | 4/1987 | Kempe | 530/307 |
| 4,720,483 | 1/1988 | Jansz et al. | 514/11 |
| 4,758,550 | 7/1988 | Cardinaux e al. | 514/12 |

FOREIGN PATENT DOCUMENTS 0197794 10/1986 European Pat. Off. .
87/01729 3/1987 World Int. Prop. O. .

OTHER PUBLICATIONS

Haruaki Yajima et al., Tetrahedron vol. 44, No. 3, 805-819, 1988.

Primary Examiner—Lester L. Lee
Assistant Examiner—A. M. Davenport
Attorney, Agent, or Firm—Kenyon & Kenyon

[57] ABSTRACT

Calcitonin derivatives wherein at least one of the first cysteine residue and the seventh cysteine residue is S-sulfonated; processes for the production of the calcitonin derivatives comprising the steps of reacting a calcitonin with a sulfite anion or both a sulfite anion and an oxidizing agent to form the S-sulfonated derivative, and recovering the sulfonated calcitonin derivative; a pharmaceutical composition comprising the S-sulfonated calcitonin derivative; and a method of treating a patient having a disease wherein a decrease of a serum calcium level is desired, by administering the S-sulfonated calcitonin derivative to the patient.

1 Claim, No Drawings

S-SULFONATED CALCITONIN DERIVATIVES

BACKGROUND OF THE INVENTION

1. Field of the Invention

The present invention relates to S-sulfonated calcitonin derivatives, a process for a production thereof, and the use thereof. The present S-sulfonated calcitonin derivatives are promising for use in the drug therapy of osteoprosis, hypercalcemia, and Paget's disease and the like, as well as for a stimulation of osteogenesis.

2. Description of Related Art

Calcitonins are well known as polypeptides exhibiting an activity of lowering a serum calcium level. Calcitonins are secreted from a thyroid gland of mammals such as humans, porcines, bovines, sheep and the like, as well as an ultimobranchial body of, for example, fowls and fishes such as salmon and eel and the like, amphibia, and reptiles and the like. These calcitonins have been isolated and purified, and their amino acid sequences determined.

Recently, various kinds of calcitonins and calcitonin-like substances prepared by chemical synthesis or gene recombination techniques have been reported, and among them, salmon calcitonins, eel calcitonin, porcine calcitonin, human calcitonin and the like have been clinically used.

All of these various kinds of calcitonins have a common structure in that they consist of 32 amino acid residues wherein the first amino acid and the seventh amino acid are L-cysteine, and mercapto radicals of the L-cysteine residues together form a disulfide bridge. It is believed that this disulfide bridge between the first amino acid and the seventh amino acid, or an ethylene linkage between these amino acids, is an essential structure for the exhibition of the biological activities of calcitonins.

Unfortunately, the presence of the disulfide bridge in question in calcitonins makes them physiochemically unstable, resulting in a degradation thereof during their purification processes and storage, as well as difficulties in their formulation. Moreover, it is believed that a short in vivo half-life of calcitonin partly results from the disruption of the disulfide bridge in question by endogeneous enzymes.

SUMMARY OF THE INVENTION

Accordingly, calcitonin derivatives which exhibit biological activities of native calcitonin, and simultaneously, are physicochemically stable, are urgently required.

The present inventors, after intensive research into the creation of calcitonin derivatives having the above-mentioned desired properties, found that an S-sulfonated calcitonin derivative is easily obtained by reacting a starting calcitonin with a compound generating sulfite ion and/or an oxidizing agent such as a compound generating tetrathionate ion n an aqueous medium, and surprisingly and unexpectedly, found that the product, i.e., S-sulfonated calcitonin derivative, exhibits biological activities of native calcitonin even though it includes neither a disulfide bridge nor an ethylene linkage between the first and seventh amino acid residues, and the product is remarkably physicochemically stable in comparison to native calcitonin.

Accordingly, the present invention provides calcitonin derivatives wherein at least one of the first cysteine residue and the seventh cysteine residue in calcitonin is S-sulfonated.

The present invention also provides a process for the production of a calcitonin derivative wherein one of the first and seventh cysteine residues in calcitonin is S-sulfonated is S-sulfonate, or salts thereof, comprising the steps of: reacting a calcitonin with sulfite anion to form a calcitonin derivative wherein one of the first cysteine residue and the seventh cysteine residue is S-sulfonate and recovering the mono S-sulfonated calcitonin derivative.

Further, the present invention providers a process for the production of a calcitonin derivative wherein both the first cysteine residue and the seventh cysteine residue in calcitonin are S-sulfonated, or salts thereof, comprising the steps of: reacting a calcitonin with sulfite anion and with a oxidizing agent to form a calcitonin derivative wherein both the first cysteine residue and the seventh cysteine residue are S-sulfonated; and recovering the diS-sulfonated calcitonin derivative.

The present invention still further provides a pharmaceutical composition comprising the above-mentioned calcitonin derivative, or pharmaceutically acceptable salt thereof, together with a conventional carrier.

The present invention also provides a method of treating a patient having a disease wherein a decrease of a serum calcium level is desired, comprising administering a calcitonin derivative, or pharmaceutically acceptable salt thereof, to the patient.

PREFERRED EMBODIMENTS OF THE INVENTION

The calcitonins used as starting materials of the present calcitonin derivatives may be any calcitonins and calcitonin derivatives prepared by any process, including extraction from calcitonin-containing tissues or organs such as the thyroid gland of mammals or ultimobrantial body of fowls and fishes, chemical synthesis and gene recombination technology, as long as they provide a biologically active S-sulfonate derivative. These calcitonins include human calcitonin, porcine calcitonin, bovine calcitonin, sheep calcitonin, fowl calcitonin, salmon calcitonin-I, salmon calcitonin-II salmon calcitonin-III and eel calcitonin; various polypeptides having an amino acid sequence different from that of a native calcitonin but exhibiting biological activities substantially equivalent to those of the native calcitonin; as well as polypeptides not exhibiting the biological activities of calcitonin but providing biologically active calcitonin derivatives after S-sulfonation. According to the present invention, salmon calcitonins, eel calcitonin, porcine calcitonin, bovine calcitonin, sheep calcitonin, fowl calcitonin, and human calcitonin are preferably used. More particularly, as a starting calcitonin of the present invention, salmon calcitonin-I and polypeptides having an amino acid sequence biologically equivalent to that of native salmon calcitonin-I are used.

The above-mentioned native calcitonins are well known and their amino acid sequences have been determined.

The present S-sulfonated calcitonin derivatives include mono S-sulfonated calcitonin derivatives wherein the first cysteine residue in a calcitonin molecule is S-sulfonated, monoS-sulfonated calcitonin derivatives wherein the seventh cysteine residue in a calcitonin molecule is S-sulfonated, and diS-sulfonated calcitonin derivatives wherein both the first cysteine residue and the seventh cysteine residue are S-sulfonated, derived from the above-mentioned various kinds of calcitonins and their derivatives. Preferably, the present sulfonated derivatives are diS-sulfonated calcitonin derivatives. A preferable example of the diS-sulfonated derivative is a salmon calcitonin-I derivative, wherein both the first and seventh cysteine residues are S-sulfonated, and is represented by the following formula:

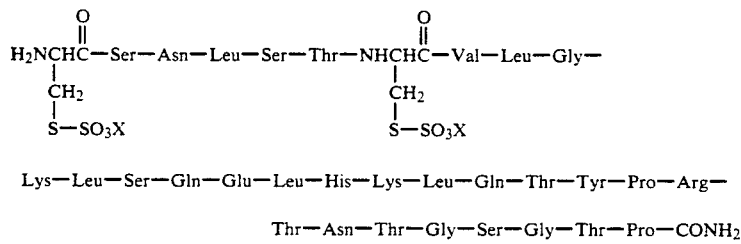

Lys—Leu—Ser—Gln—Glu—Leu—His—Lys—Leu—Gln—Thr—Tyr—Pro—Arg—

Thr—Asn—Thr—Gly—Ser—Gly—Thr—Pro—CONH$_2$ wherein X represents hydrogen or alkaline metal.

The present invention also provides salts of the above-mentioned S-sulfonated calcitonin derivatives. The present calcitonin derivative salts include metal salts, for example, alkaline metal salts such as lithium salt, sodium salt and potassium salt, alkaline earth metal salts such as calcium salt and magnesium salt, as well as ammonium salt.

For the production of the present S-sulfonated calcitonin derivatives, a starting calcitonin is reacted with a sulfite anion according to the following reaction scheme [I]:

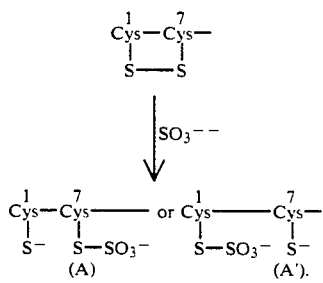

According to the above-mentioned reaction, mono-sulfonated calcitonin derivatives are generated.

For the production of a diS-sulfonated calcitonin derivative, the above-mentioned reaction is carried out in the presence of an oxidizing agent, in addition to the sulfite anion. Namely, a monoS-sulfonated intermediate, for example, derivative (A) generated in the above-mentioned reaction, may be oxidized to form an intermediate (B) wherein two monoS-sulfonated calcitonin molecules are intermolecularly linked via a disulfide linkage according to the following reaction scheme [II]:

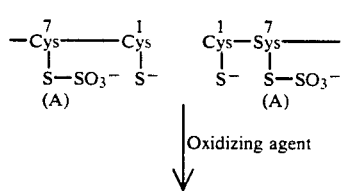

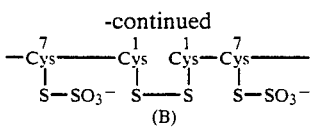

Next, the intermediate dimer (B) is reacted with a sulfite anion, as follows [III]:

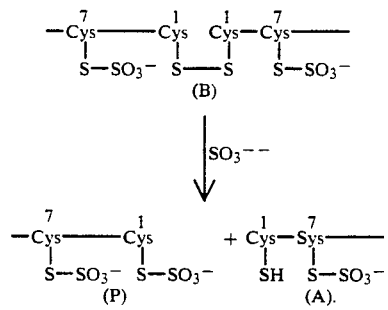

By allowing a chain reaction consisting of reactions [II] and [III], a desired diS-sulfonated calcitonin derivative (P) is obtained.

Alternatively, the above-mentioned monoS-sulfonated intermediate may be reacted with a tetrathionate ion to form an S-thiosulfate intermediate (C), which is then cleaved to provide a di-sulfonated calcitonin derivative (P) and thiosulfate ion, according to the following reaction scheme (IV):

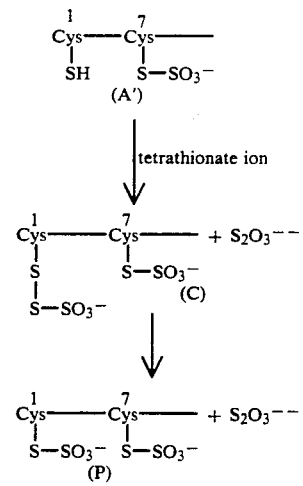

In the above-mentioned reactions [I] and [III], the sulfite anion may be provided by any source which can provide sulfide anion in a used reaction medium. Preferable sulfite anion sources are, for example, sulfurous acid and salts thereof such as sodium sulfite, sodium bisulfite, potassium sulfite and potassium bisulfite; metasulfurous acid and salts thereof, such as sodium metasulfite, potassium metasulfite; and 5-sulfothio-2-nitro-benzoic acid and salts thereof.

In the above-mentioned reaction [II], the oxidizing agents are, for example, tetrathionate ion, oxygen, or cupric ion. As sources of the tetrathionate ion, any reagents which provide tetrathionate ions in a used reaction medium may be used. Preferable tetrathionate ion sources are, for example, tetrathionic acid and tetrathionate salts, for example, alkaline metal tetrathionate such as sodium tetrathionate and potassium tetrathionate. A convenient source of oxygen is air, and the source of cupric ion is, for example, cupric sulfate and cupric chloride.

In order to prepare monoS-sulfonated calcitonin derivatives, a sulfite ion source is preferably used in an amount which provides a ratio of one mole or more moles of sulfite ion to one mole of a calcitonin. And, for the purpose of preparation of diS-sulfonated calcitonin derivatives, a sulfite ion source is preferably used in a ratio of two mole or more and an oxidizing agent is preferably used in a ratio of one mole or more to one mole of a calcitonin, respectively.

The reaction is preferably carried out in an aqueous solution, for example, an aqueous buffer solution such as Tris-HCl buffer solution, phosphate buffer solution, tartarate buffer solution or Good's buffer solution. The reaction medium may contain a protein denaturating agent such as urea or guanidine, although medium which does not contain such a protein denaturating agent is advisable.

The reaction is preferably carried out at a temperature not exceeding 50° C., usually at a room temperature. A pH value of a reaction medium is preferably between 6.0 and 10.0.

The reaction time depends on various factors such as the kind of calcitonin to be S-sulfonated, amounts of reagents used, reaction temperature, and the presence or absence of a protein-denaturating agent such as urea and the like. Usually the reaction time is about 10 minutes to 180 minutes.

The order of addition of the reactants is not critical.

The S-sulfonated calcitonin derivative generated according to the above-mentioned processes can be isolated and purified by a conventional procedure used for the isolation and purification of polypeptides. Such a conventional process may comprise methods using the difference of solubility of a desired product and impurities, such as salting out and solvent-precipitation; methods using the difference of a molecular weight of a desired product and impurities, such as dialysis, ultrafiltration, gel-filtration and electrophoresis such as SDS-polyacrylamide gel electrophoresis; methods using the difference of electric charges, such as ion-exchange chromatography and ion-exchange high performance liquid chromatography; methods using a specific affinity such as affinity chro methods using the difference of hydrophobicity, such as reverse phase high performance liquid chromatography methods using the difference of isoelectric points, such as isoelectric focusing; and any combination thereof. The present sulfonated calcitonin derivatives are advantageous in that, since they do not have a disulfide bridge between the first and the seventh cysteine residues, they are remarkably stable during the isolation and purification thereof.

The present sulfonated calcitonin derivatives obtained as described above may be lyophilized, if necessary, to be stored in a form of a solid such as a powder. For the lyophilization, a stabilizing agent such as sorbitol, mannitol, dextrose, maltose, glycerol, human serum albumin (HSA) or the like, may be added.

The S-sulfonated calcitonin derivatives of the present invention exhibited an activity of lowering a serum calcium level, during animal experiments using rats as described in detail hereinafter. Accordingly, in the same manner as in conventional calcitonins, the present S-sulfonated calcitonin derivatives can be used for pharmaceuticals, for example, for the drug therapy or alleviation of symptoms of various diseases where a decrease of the serum calcium level is desired. More specifically, the present S-sulfonated calcitonin derivatives can be used for the drug therapy of all kinds of bone diseases, where a fixation of a serum calcium to bone is desired; osteoporosis stemming from various causes, such as adrenocortical hormone therapy, immobilization, or post menopause or after receiving an external wound; fracture of a bone; osteomalacia; rickets; renal osteodystrophy; hypercalcemia; Paget's disease, and the like.

The present S-sulfonated calcitonin derivatives are used in a pharmaceutically acceptable formulation which is suitable for oral administration or parenteral administration such as intravenous, intramuscular, subcutaneous, transdermal, rectal, per respiratory tract such as or intranasal administration, perlung or intra articular administration, or for administration carried out by an ionophoretic device.

Since the present S-sulfonated calcitonin derivatives are remarkably stable, as described above, they can be formulated in the form of a liquid such as a solution or suspension. This is one of the most important advantages of the present calcitonin derivatives over conventional calcitonin including native calcitonins and their derivatives, which cannot be formulated in a liquid form due to their low storage stability.

EXAMPLES

The present invention will now be further illustrated by, but is by no means limited to, the following Examples.

EXAMPLE 1

Production of diS-sulfonated salmon calcitonin-I (1)

First, 1 mg of salmon calcitonin-I was dissolved in 1 ml of a sulfonation medium comprising 7 M urea, 0.1 M sodium sulfite, and 0.01 M sodium tetrathionate in 0.5 M Tris-HCl (pH 8.2) buffer, and the mixture was reacted at 37° C. for one hour. The reaction mixture was dialyzed three times against 1 l each of purified water at 4° C., and the dialyzated inner solution was lyophilized to obtain 1 mg of S-sulfonated salmon calcitonin-I.

The high purity of the resulting S-sulfonated salmon calcitonin-I was confirmed by reverse high performance liquid chromatography (reverse HPLC), and it was confirmed that the resulting S-sulfonated salmon calcitonin I is really an diS-sulfonated salmon calcitonin I formed by a cleavage of the disulfide bridge between the first cysteine residue and the seventh cysteine residue and sulfonation of two sulfur atoms of corresponding cysteine residues, as shown by the following tests:

(1) Analysis of N-terminal amino acid sequence

This analysis shows that an amino acid sequence of the product is the same as that of native salmon calcitonin-I except for the first and seventh cysteine residues, which cannot be detected by this method.

(2) Sulfonation using [$^{35}$S]-labelled $Na_2SO_3$

Sulfonation of salmon calcitonin-I by [$^{35}$S]-labelled $Na_2SO_3$ provided a sulfonated product containing two moles of -$^{35}SO_3$ per one mole of salmon calcitonin-I.

(3) Confirmation by derivatization using dithiothreitol

A compound formed by treating salmon calcitonin-I with dithiothreitol was identical to a compound formed by treating the above-mentioned sulfonated product in a reverse HPLC pattern. Note, dithiothreitol reduces both the disulfide bond and -sulfonate group to provide a sulhydryl group.

(4) Amino acid composition

An analysis of the amino acid composition of the diS-sulfonated salmon calcitonin I showed the presence of two moles of S-sulfonated cystein in one mole of the diS-sulfonated salmon calcitonin-I.

(5) FAB-Mass analysis

Fast atom bombardment (FAB) mass spectrometry of the diS-sulfonated salmon calcitonin I using a mass spectrometer (JMS-S × 10$^2$, Nippon Denshi, Japan) provided an m/e peak at 3594.5.

Since the molecular weight of native salmon calcitonin-I is 3432.4, the above-mentioned data suggests that two cystein residues have been S-sulfonated in the diS-sulfonated salmon calcitonin I.

EXAMPLE 2

Production of diS-sulfonated calcitonin-I (2)

The same procedure as described in Example 1 was repeated except that a sulfonation medium comprising 7 M urea and 0.1 M sodium metasulfite in 0.5 M Tris-HCl (pH 8.2) buffer was used, to obtain a diS-sulfonated salmon calcitonin-I.

EXAMPLE 3

Production of diS-sulfonated calcitonin-I (3)

The same procedure as described in Example 1 was repeated except that a sulfonation medium comprising 5-sulfothio-2-nitro-benzoic acid (Thannhouser et al., Biochemistry 24, 7681–7688, 1985) in 0.5 M Tris-HCl (pH 8.2) buffer was used, to obtain a diS-sulfonated salmon calcitonin-I derivative.

EXAMPLE 4

Production of diS-sulfonated human calcitonin-I (4)

First, 0.5 mg of human calcitonin was dissolved in 0.5 ml of a sulfonation medium comprising 7 M urea, 0.1 M sodium sulfite, and 0.01 M sodium tetrathionate in 0.5 M Tris-HCl (pH 8.2) buffer, and the mixture was reacted at 37° C. for 30 minutes.

The reaction mixture was dialyzed three times against 1 l each of purified water, and the dialyzed inner solution was lyophilized to obtain 0.5 mg of diS-sulfonated human calcitonin.

EXAMPLE 5

Biological activities of diS-sulfonated salmon calcitonin-I

Experimental method

Wistar male rats having a body weight of 120 to 140 g were starved overnight, and phosphate-buffered saline [PBS(-)]described hereinafter, diS-sulfonated salmon calcitonin-I solution, or salmon calcitonin-I solution was subcutaneously injected in the backs of the animals in an amount of 1 ml/kg. One hour and two hours after the injection, about 0.2 ml of a blood sample was obtained from ophthalmic vein. The blood sample was centrifuged at 3000 rpm for 10 minutes by a centrifugation (Hitachi, SCT5BA) to obtain a supernatant as a serum fraction.

The serum calcium concentration was determined by the o-cresolphthalein complexon (OCPC) method using a commercial calcium assay reagent (Ca SET, Iatron). Namely, 50 μl of serum was put into a test tube, to which was added 0.5 ml of a color-developing reagent (RM117-2) comprising o-cresolphthalein complexon and 8-hydroxyquinoline, and the mixture was stirred. Next, to the mixture was added 5.0 ml of monoethanolamineborate buffer (RM117-1) and the mixture was stirred. Within 90 minutes, the absorbance at 575 nm was measured by an auto-recording spectrophotometer (MPS-2000, Shimazu Seisakusho, Japan). The calcium concentration was calculated from the absorbance. The PBS(-), the diS-sulfonated salmon calcitonin-I solution, and the salmon calcitonin-I solution used in the above-mentioned experiment were prepared as follows.

a) PBS(-): 9.6 g of Dulbecco's PBS(-) (Nissui Seiyaku, Japan) was dissolved in 1 l of double distilled water.

b) diS-sulfonated salmon calcitonin-I solution: diS-sulfonated salmon calcitonin-I was diluted with the above-prepared PBS(-) to make a concentration of the derivative 31.25 ng/ml, 62.5 ng/ml, 125 ng/ml, and 250 ng/ml.

c) Salmon calcitonin-I solution: salmon calcitonin-I (Peninsula Laboratories Inc.) was diluted with the above-prepared PBS(-) to make a concentration of the salmon calcitonin-I 31.25 ng/ml, 62.5 ng/ml, 125 mg/ml, and 250 ng/ml.

Experimental results

The results are shown in Table 1.

TABLE 1

| | Change in serum calcium level (mg/100 ml)[1] | | | | |
|---|---|---|---|---|---|
| | Amount of test compound injected (ng/kg) | | | | |
| Test compound | 0 (control)[2] | 31.25 | 62.5 | 125 | 250 |
| | (One hour after injection) | | | | |
| diS-sulfonated salmon calcitonin-I | 9.38 ± 0.38 | 9.39 ± 0.28 | 8.89 ± 0.13 | 7.86 ± 0.18* | 7.35 ± 0.16* |
| Salmon calcitonin-I | 9.38 ± 0.38 | 9.52 ± 0.19 | 9.44 ± 0.19 | 8.01 ± 0.23* | 7.77 ± 0.02* |
| | (Two hours after injection) | | | | |
| diS-sulfonated salmon calcitonin-I | 9.16 ± 0.20 | 9.58 ± 0.19 | 9.36 ± 0.45 | 9.62 ± 0.12 | 7.49 ± 0.24* |

TABLE 1-continued

| Test compound | Change in serum calcium level (mg/100 ml)[1] | | | | |
|---|---|---|---|---|---|
| | Amount of test compound injected (ng/kg) | | | | |
| | 0 (control)[2] | 31.25 | 62.5 | 125 | 250 |
| Salmon calcitonin-I | 9.16 ± 0.20 | 9.60 ± 0.25 | 9.57 ± 0.18 | 9.00 ± 0.28 | 7.25 ± 0.14* |

[1]Serum calcium level is expressed by average ± standard deviation obtained from 6 animals.
[2]Control means PBS(−) alone injected.
[3]*Significant difference in comparison to control by at most 0.1% risk.

As seen from Table 1, the diS-sulfonated salmon calcitonin-I of the present invention significantly decreased the serum calcium level at a dose of 125 ng/kg or more one hour after the injection, and at a dose of 250 ng/kg two hours after the injection, in comparison to a control wherein PBS(-) alone was injected. The decrease of serum calcium levels one and two hours after the injection of the diS-sulfonated salmon calcitonin-I is substantially equivalent to those after an injection of salmon calcitonin, revealing that the present diS-sulfonated calcitonin derivatives have substantially the same activity of decreasing the serum calcium level as that of a corresponding salmon calcitonin.

EXAMPLE 6

Stability test in frozen state

First, 50 μg each of the diS-sulfonated salmon calcitonin-I and salmon calcitonin-I were separately dissolved in 100 μl of 2.5 mM citrate (pH 2.8) buffer, and the solutions were frozen and stored at −80° C. After 5 months, the frozen samples were thawed, and residual diS-sulfonated salmon calcitonin-I and salmon calcitonin-I were measured by reverse HPLC. The results are shown in Table 2.

TABLE 2

| Test compound | Residual amount (%) 5 months |
|---|---|
| diS-sulfonated salmon calcitonin-I | >99.5 |
| Salmon calcitonin-I | 50 |

As seen from Table 2, the present diS-sulfonated calcitonin-I was remarkably stable in the frozen state, compared to the corresponding native calcitonin-I.

EXAMPLE 7

Stability test in liquid form

First, 50 μg each of the diS-sulfonated salmon calcitonin-I and salmon calcitonin-I were separately dissolved in 100 μl of 50 mM Tris-Hcl buffer solution (pH 7.2), and the solutions were stored at 37° C. After 2 weeks, the residual diS-sulfonated salmon calcitonin-I and salmon calcitonin-I were measured by reverse HPLC. The results are shown in Table 3.

TABLE 3

| Test compound | Residual amount (%) after 2 weeks |
|---|---|
| diS-sulfonated salmon calcitonin-I derivative | 92.1 |
| Salmon calcitonin-I | 69.9 |

As seen from Table 3, the present diS-sulfonated calcitonin derivative is remarkably stable in a solution, compared to the corresponding native salmon calcitonin-I.

We claim:

1. A method for treating a patient having a disease wherein a decrease of serum calcium is desired, comprising the steps of: administering to the patient a composition comprising a pharmaceutically acceptable carrier and a compound selected from the group consisting of calcitonin derivatives, and pharmaceutically acceptable salts thereof, including at least one of a S-sulfonated cysteine residue in the first position and a S-sulfonated cysteine residue in the seventh position.

* * * * *